US 9,062,904 B2

(12) United States Patent
Doty

(10) Patent No.: US 9,062,904 B2
(45) Date of Patent: Jun. 23, 2015

(54) STABILIZING CONTROL OF A SATURATED COLD GAS STREAM

(71) Applicant: Doty Scientific, Inc., Columbia, SC (US)

(72) Inventor: F David Doty, Columbia, SC (US)

(73) Assignee: Doty Scientific, Inc., Columbia, SC (US)

( * ) Notice: Subject to any disclaimer, the term of this patent is extended or adjusted under 35 U.S.C. 154(b) by 0 days.

(21) Appl. No.: 14/239,094

(22) PCT Filed: Sep. 10, 2013

(86) PCT No.: PCT/IB2013/058437
§ 371 (c)(1),
(2) Date: Feb. 14, 2014

(87) PCT Pub. No.: WO2014/064550
PCT Pub. Date: May 1, 2014

(65) Prior Publication Data
US 2014/0216080 A1    Aug. 7, 2014

Related U.S. Application Data

(60) Provisional application No. 61/717,512, filed on Oct. 23, 2012.

(51) Int. Cl.
*F25B 19/00* (2006.01)
*F17C 13/00* (2006.01)
(Continued)

(52) U.S. Cl.
CPC ............ *F25D 3/10* (2013.01); *F25J 1/0015* (2013.01); *F25J 1/0276* (2013.01); *F25J 1/0257* (2013.01);
(Continued)

(58) Field of Classification Search
CPC .......... F25D 3/10; F25J 1/0072; F25J 1/0015; F25J 1/0276; F25J 1/0257; H01L 23/445; F17C 2227/0309; F17C 2227/0367; F17C 2227/0369; F17C 2227/0372; F17C 2227/0374
USPC .................................. 62/51.1, 50.7, 606, 616
See application file for complete search history.

(56) References Cited

U.S. PATENT DOCUMENTS 4,456,882 A    6/1984   Doty
4,511,841 A    4/1985   Bartuska
(Continued)

OTHER PUBLICATIONS

R. D. Kendrick et al., A Stratagem for Low-Temperature Magic-Angle Spinning Using Nitrogen Spinning Gas, Jun. 4, 1985.*
(Continued)

*Primary Examiner* — Frantz Jules
*Assistant Examiner* — Webeshet Mengesha
(74) *Attorney, Agent, or Firm* — Oppedahl Patent Law Firm LLC

(57) ABSTRACT

An improved method of supplying pressurized cold gas consistently of predominately $N_2$ and He at low flow rate (typically under 1 g/s) with a desired $N_2$ liquid fraction to an instrument requiring such is disclosed. Pressurized ultra-dry nitrogen gas of a controlled mass-flow rate is cooled inside fine coils bathed in liquid nitrogen to condense it to a vapor fraction less than about 20% and typically under 3%. A second gas stream consisting of predominately nitrogen plus helium, supplied from a controlled pressure, is cooled in a separate set of coils to an exit mean temperature significantly above the temperature of saturated nitrogen vapor in this mixture. The fluid from the first (condensed) mixture is injected into the cooled gas from the second mixture and transferred through a thermally insulated line to the input of the instrument needing a supply of cold gas of a target vapor fraction.

1 Claim, 4 Drawing Sheets

(51) Int. Cl.
*F25D 3/10* (2006.01)
*F25J 1/00* (2006.01)
*F25J 1/02* (2006.01)
*F17C 7/04* (2006.01)
*F17D 1/04* (2006.01)
*F17D 1/08* (2006.01)
*G01R 33/31* (2006.01)

(52) U.S. Cl.
CPC .................. *F25J 1/0072* (2013.01); *F17C 7/04* (2013.01); *F17C 13/00* (2013.01); *F17D 1/04* (2013.01); *F17D 1/082* (2013.01); *G01R 33/31* (2013.01)

(56) References Cited

U.S. PATENT DOCUMENTS

| | | | |
|---|---|---|---|
| 4,940,942 A | 7/1990 | Bartuska | |
| 5,202,633 A | 4/1993 | Doty | |
| 5,508,615 A | 4/1996 | Doty | |
| 7,151,374 B2 | 12/2006 | Doty | |
| 7,170,292 B2 | 1/2007 | Doty | |
| 7,282,919 B2 | 10/2007 | Doty | |
| 7,600,387 B2* | 10/2009 | Hume et al. | 62/52.1 |
| 7,915,893 B2 | 3/2011 | Shevgoor | |
| 2006/0097146 A1 | 5/2006 | Strobel | |
| 2007/0024284 A1 | 2/2007 | Roth | |
| 2009/0183860 A1* | 7/2009 | Krencker et al. | 165/164 |
| 2011/0173996 A1 | 7/2011 | Glajchen et al. | |
| 2012/0242335 A1 | 9/2012 | Schett et al. | |

OTHER PUBLICATIONS

Hans Förster, AVANCE DMX/DSX Spectrometers, Sep. 23, 1996.*
Alexander B. Barnes et al., Cryogenic sample exchange NMR probe for magic angle spinning dynamic nuclear polarization, Oct. 19, 2010.*
International Search Report mailed Feb. 6, 2014.
Written Opinion mailed Feb. 6, 2014.
Doty et al in J. Magn. Reson. 182 (2006) pp. 239-253.
Thurber and Tycko in J. Magn. Reson.195 (2008) 179-186.

* cited by examiner

STABILIZING CONTROL OF A SATURATED COLD GAS STREAM

FIELD OF THE INVENTION

The field of this invention is an improved method of providing a stream of cold gas to the inlet of a Magic Angle Spinning (MAS) Nuclear Magnetic Resonance (NMR) probe with substantially improved temperature and flow stability when a primary component in the gas stream is near its saturated vapor temperature, typically in the range of 75-110 K.

BACKGROUND OF THE INVENTION

Most modern techniques for improving spectral resolution in NMR of solids include extremely rapid spinning of the sample at the "Magic Angle" (the zero of the second Legendre polynomial, 54.7°) with respect to $B_0$. If the rotational rate is fast compared to chemical shift anisotropies and dipolar couplings (in units of Hz), the resolution is dramatically improved—often by two or three orders of magnitude. In many cases, it is important to be able to obtain the NMR data—often used to determine molecular structural information—on samples that are at very low or very high temperatures.

A technique sometimes capable of increasing signal to noise (S/N) ratio in MAS by one to three orders of magnitude in solid samples at low temperatures, known as Dynamic Nuclear Polarization (DNP), combines millimeter-wave (mmw) irradiation of the sample with NMR detection, where the mmw frequency is about 660 times the proton NMR resonant frequency. However the technique seldom works well above 120 K. Often, for each 10 K reduction in sample temperature between 120 K and 30 K, the S/N enhancement increases by a factor of two and the required mmw irradiation power decreases by a similar factor. Hence, there is strong motivation for improving MAS at temperatures below 120 K. In most cases, DNP works best at spinning rates between 4 kHz and 9 kHz, which is much less than desired for many other MAS techniques.

In U.S. Pat. No. 4,456,882, I disclose a high-speed NMR MAS ceramic sample spinner using radial bas bearings, a solid lubricated point bearing at the bottom, and impulse turbine drive at the top. In U.S. Pat. No. 4,511,841, Bartuska discloses a modified Beams-type Bernoulli out-flow bearing-drive for MAS; and in his later U.S. Pat. No. 4,940,942, he discloses a method of providing variable temperature (VT) operation for the sample using three gas stream—one for the sample region, one for the radial bearings at each end, and one for axial Bernoulli out-flow bearing and drive at the bottom. In U.S. Pat. No. 5,508,615, I disclose a method of suppressing whirl instability in the radial bearings at very high surface speeds in MAS and improving the stability of balanced axial hydrostatic bearings, similar to the one used in the HT-MAS probe disclosed in U.S. Pat. No. 5,202,633. In U.S. Pat. No. 7,151,374, I disclose a method of improving S/N in triple-tuned MAS probes by cooling the auxiliary RF tuning coils to about 100 K with a stream of cold $N_2$ gas. In U.S. Pat. No. 7,170,292, we disclose a novel Bernoulli inflow axial bearing that is particularly advantageous for MAS when vacuum insulation is required between the rotor and the sample coils. This is advantageous in the CryoMAS probe we disclose in U.S. Pat. No. 7,282,919, or when the spinner needs to be hermetically sealed for operation inside an external high vacuum region, as disclosed in our improved CryoMAS probe in U.S. Pat. No. 7,915,893.

In all of the above cases except Bartuska's U.S. Pat. No. 4,940,942, the sample temperature is established predominately by the bearing gas temperature plus effects from frictional heating and RF heating, which is discussed in more detail by Doty et al in J. Magn. Reson. 182 (2006) pp 239-253. Bartuska correctly claims that using a separate cold gas stream for the sample VT with warm gas for the bearing and drive permits faster sample spinning at low temperatures, but the three-stream approach comes with its own set of problems: (1) the rotor must be much longer to reduce thermal gradients within the sample, which has prevented it from being used in narrow-bore (NB) magnets or even in wide bore (WB) magnets with sample eject; (2) access to the rf coils is considerably more complicated, and this has apparently prevented the advantageous use of multiple sample rf coils in low-temperature (LT) MAS probes with 3-stream operation. See, for example, the very impressive LT-MAS work described by Thurber and Tycko in J. Magn. Reson. 195 (2008) 179-186, in which they were able to achieve 6.7 kHz MAS at 25 K with a 4-mm rotor inside a probe of 88-mm OD in a 9.4-T magnet using a spinner similar to that of U.S. Pat. No. 4,940,942.

An estimated 85% of the NMR magnets sold between 2002 and 2012 have bores inside their room-temperature (RT) shims of less than 45 mm, and most of those have been 40 mm. Most (perhaps almost all) of the MAS probes for such have utilized two gas streams—one supplying bearing pressure and largely establishing sample temperature, and the other supplying pressure to the drive turbines. Most of these probes have been specified by their manufacturer (such as Bruker, Agilent, or JEOL) as being able to spin at temperatures down to around 200 K. A substantial number of probes by another manufacturer (Doty Scientific) have been specified as being able to spin at temperatures down to 110 K to 160 K using $N_2$, but it has always been very difficult to obtain stable spinning at acceptable speeds at temperatures below 130 K for extended periods of time with known $N_2$ gas-cooling technology—and sometimes difficult even at 180 K.

Prior Art MAS Cold Gas Supplies. For the past three decades, most MAS cold-gas supply systems have been similar in general respects to that shown in FIG. 1. Pressurized RT $N_2$ gas is pre-cooled by boil-off gas flowing up the neck of the cryostat, and then cooled by a cooling coil immersed in liquid nitrogen (LN2) in the LN2 cryostat (often 50-liter capacity).

The biggest limitation with prior art LT-MAS using two N2 gas streams comes not from the spinner or probe design, but from the cold gas supply to the probe. It has not been practical to reduce heat leaks in the flow between the spinner gas cooling coil in the LN2 cryostat and the spinner assembly to less than about 15 W using standard vacuum-insulated transfer lines and couplings. Typical losses (for either the bearing or the drive stream) are ~2.5 W in the connections at each end of the vacuum-insulated transfer line, ~3 W per additional connection (in the base of the probe and at the top of the top of the LN2 cryostat), ~3 W in the flexible vacuum insulated transfer line, and ~1 W miscellaneous, totaling ~15 W for each stream.

However, the bearing gas flow rate needed for a typical 4-mm rotor, for example, is only about 0.25 g/s at ~110 K for ~5 kHz spinning. At that flow rate and heat leak, the temperature of the bearing gas—if no liquid is present—increases by 56 K between the cooling coil in the liquid nitrogen cryostat and the spinner. If nitrogen gas leaves the cooling coil just above its boiling point at 220 kPa (which is 84 K), it arrives at the spinner at 140 K. The problem is worse with smaller spinners, as the gas flow rate is lower.

The temperature rise during the transfer can be reduced by deliberately adding a vent hole near the spinner to increase the flow rate, but even with a leak three times the normal bearing flow, the minimum bearing gas temperature entering the spinner will be ~105 K, and the large additional gas flow is not desired, particularly for long runs.

To achieve bearing-gas temperatures below ~140 K at low flow rates it is necessary to have a liquid fraction in the gas leaving the cooling coil and to use its heat of vaporization to balance the heat leaks. At a liquid fraction of 30% for 0.25 g/s $N_2$, the heat of vaporization of the liquid is 14 W—about what is needed to balance the heat leaks through the vacuum-insulated transfer line, couplings, and dewared transfer line inside the probe. So if it were possible to achieve a 30% liquid fraction (by mass, not volume) of $N_2$ leaving the cooling coil at 84 K and 220 kPa, the 0.25 g/s flow should arrive at the spinner as 100% gas at 84 K. Unfortunately, this is an impossible control problem by prior methods, as explained in the following discussion.

Oscillating Flow with Conventional Two-phase Cooling. If liquid droplets reach an orifice in the spinner assembly (or a leak along the way), the mass flow increases dramatically. (The viscosity of liquid nitrogen is an order of magnitude greater than that of the gas, but the density of the liquid may be two orders of magnitude greater at typical conditions.) At the higher flow rate, the pressure in the transfer line from the gas cooling coil plummets, causing the temperature to drop and the flow rate through the cooling coil in the LN2 cryostat to jump. Since there is a significant liquid fraction in the fluid in the transfer line, its temperature stays pegged at the boiling point of $N_2$ at the pressure in the line until the liquid fraction is gone.

If a vent hole has been added near the spinner with leak rate similar to the bearing flow, the total flow needed (for the typical 4-mm spinner) is ~0.5 g/s, and the ideal starting liquid fraction of $N_2$ should be ~15%. If the mixture in the transfer line is 15% liquid at 0.5 g/s, it runs through the transfer line in about half a minute for the typical case. However, when liquid is at the bearing orifices, the flow rate is much higher than if all gas, so the mixture coming from the cooling coil at the lower transfer-line pressure would be at a slightly lower temperature but of decreased liquid fraction (because the cooling capacity of the cooling coil is less at a temperature closer to the reservoir temperature of 77 K in the 50-L cryostat).

So the liquid fraction in the bearing gas leaving the cooling coil is now insufficient to prevent a substantial rise in its temperature from the heat leaks during the transfer. By the time the new mixture gets to the stator, it is above the liquid boiling point, so the mass flow drops because it contains no liquid. The bearing pressure then jumps, the liquid in transit stops vaporizing, and the temperature jumps. The liquid fraction produced in the cooling coil also jumps (because the flow rate has dropped), the transfer line begins filling again with a mixture of higher liquid fraction, and the cycle then repeats when the high-liquid-fraction fluid gets to the stator.

Some positive feedback (the basic cause of instability) is also present in the system even without liquid flow through the stator (or leaks) since the gas viscosity decreases and its density increases as the temperature decreases, but this control problem is manageable until liquid droplets get to leaks or bearing holes.

Barnes et al in J Magn. Reson 198 (2009) pp. 261-270, describe a method of addressing what they see as the root of the instability problem—condensation in the cooling coil. In essence, they maintain the LN2 in the cryostat bathing the cooling coil at a pressure higher than the maximum pressure inside the cooling coil. In this way, the temperature of the LN2 is easily maintained above that which leads to condensation inside the cooling coil. While they report some success in improving stability, it should be noted that their magnet RT bore is 130 mm, the probe is entirely enclosed in a dewar of 127 mm OD, and extraordinary measures are taken to minimize heat leaks into the cold-gas transfer lines. Apparently, they have been able to reduce heat leaks sufficiently to avoid the need for a significant liquid fraction in the cold gas, but such measures are not possible in most laboratories.

SUMMARY OF THE INVENTION

An improved method of supplying pressurized cold gas consistently of predominately $N_2$ and He at low flow rate (typically under 1 g/s) with a desired $N_2$ liquid fraction to an instrument requiring such is disclosed. Pressurized ultra-dry nitrogen gas of a controlled mass-flow rate is cooled inside fine coils bathed in liquid nitrogen to condense it to a vapor fraction less than about 20% and typically under 3%. A second gas stream consisting of predominately nitrogen plus helium, supplied from a controlled pressure, is cooled in a separate set of coils to an exit mean temperature significantly above the temperature of saturated nitrogen vapor in this mixture. The fluid from the first (condensed) mixture is injected into the cooled gas from the second mixture and transferred through a thermally insulated line to the input of the instrument needing a supply of cold gas of a target vapor fraction.

DETAILED DESCRIPTION

Controlled Liquid Injection into a Chilled Gas Stream. The inherently unstable two-phase flow of the prior art can be solved by implementing controlled LN2 injection into cold gas of essentially zero liquid fraction (i.e., dry), as the two streams are separately controllable by common methods.

For illustrative purposes herein, the instrument requiring pressurized cold gas is assumed to be a typical MAS or MAS-DNP probe requiring cold spinner bearing gas and possibly cold spinner drive gas. The required $N_2$ bearing gas flow rate will typically be in the range of 0.1-1 g/s at pressure in the range of 140-350 kPa for spinning speeds in the range of 4-20 kHz with rotor sizes of 2-4 mm for temperatures below 120 K. The required drive flow is usually several times higher than the bearing flow but at similar pressures. It is usually desirable to spin at a constant speed and temperature, which requires constant pressures, densities, and temperatures for the bearing and drive gas entering the spinner.

As the heat leak rates between the gas cooling coil and the MAS probe are normally essentially constant after equilibrium, the LN2 injection rate into the gas stream normally needs to be essentially constant, and thus independent of the pressure in the line where it is injected.

From both a temperature and a spinning stability perspective, it would also help to maintain a nearly constant pressure in the transfer line, as the temperature of the two-phase flow at the point where the last drop of liquid vaporizes is essentially determined by the pressure at the point. If liquid droplets get to the stator, there is a dramatic increase in flow rate through the gas cooling coil when the droplets get to the stator—as explained earlier. If the gas leaving the cooling coil is always above the condensation temperature (i.e., zero liquid fraction), then when its flow rate through the cooling coil increases its temperature also rises, but not by much. (The gas temperature increase is small because the higher flow increases the heat transfer coefficient, and the temperature difference driving the final heat transfer also increases.)

Figure 1:
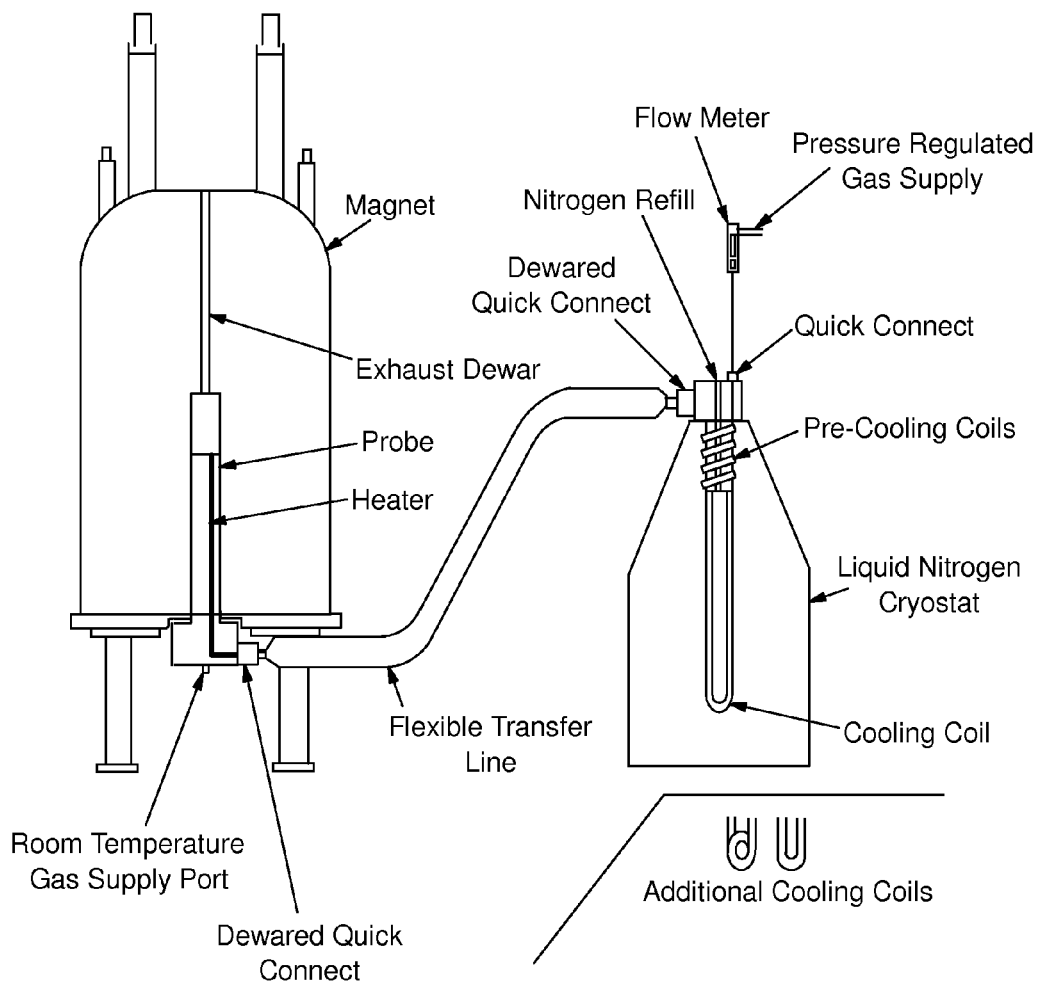
FIG. 1 is a schematic depiction of the prior art.
Figure 2:
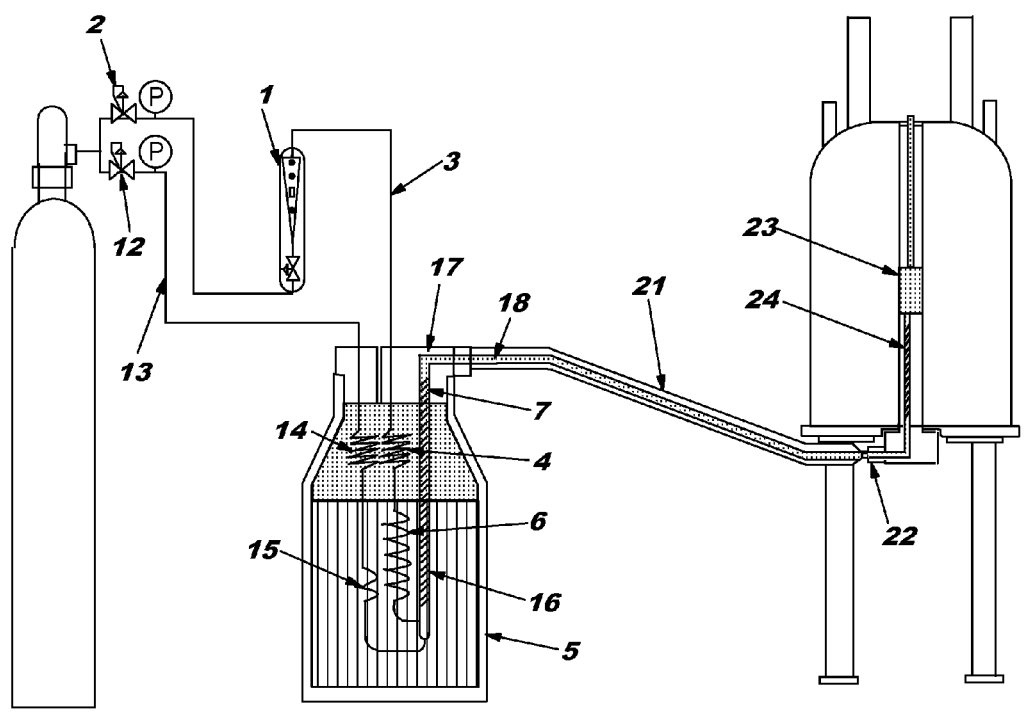
FIG. 2 is a schematic depiction of the novel LN2-injected method.

Constant LN2 Injection Flow. A schematic of the inventive method is shown in FIG. 2. The easiest way to achieve adjustable mass flow that is nearly independent of the outlet pressure is by throttling gas flow through an adjustable needle valve 1 from a inlet pressure regulator 2 such that the inlet pressure to the needle valve is well above its outlet pressure, ideally by a factor greater than 2.5, as the flow through the valve will then be sonic limited and quite independent of its outlet pressure. For sufficient liquid injection into the cold gas stream to balance heat leaks in typical transfers, a typical liquid injection flow rate of 0.03-0.3 g/s is needed. Some additional amount of liquid injection may also be needed for final cooling of the chilled gas, as will be seen. The total desired liquid injection rate is established by valve 1 controlling the $N_2$ liquefaction gas mass flow rate.

The RT $N_2$ from valve 1 is conveyed through liquefaction-supply tube 3 to the liquefaction pre-cooling coil 4, preferably in the neck of the LN2 cryostat 5 for pre-cooling by the boil-off gas, similar to the prior art.

The inlet pressure to the $N_2$ liquefaction pre-cooling coil 4 typically needs to be 200-400 kPa to overcome various pressure drops and still be sufficient for the intended use, so this means the feed gas to the valve 1 that establishes this flow should preferably be over 400-1000 kPa for the mass flow rate to not increase significantly if the outlet pressure of valve 1 drops (as for the reasons discussed earlier). In practice, a significantly lower supply pressure can usually be used with fully adequate flow rate stability. Alternatively, a modulated-valve mass-flow-controller could be used to maintain the desired nitrogen flow rate into the condensing stream with even lower supply pressure.

The pre-cooled nitrogen then proceeds to condensing coil 6 that is immersed in the LN2 in the cryostat. Coil 6 is sized such that heat transfer is sufficient to condense most—often all—of the nitrogen flowing through it. This is not difficult, as the nitrogen inside the tube is pressurized and thus condenses at a temperature typically 3-10 K above the boiling point of the LN2 in the cryostat, which is near atmospheric pressure. The condensing coil will have typical inside diameter (I.D.) between 0.3 mm and 3 mm. The largely liquefied stream is subsequently ducted to the top of the cryostat through LN2 duct 7, from which it flows into the chilled gas stream, as described next.

The Chilled Gas Stream. RT gas—usually high purity $N_2$, but possibly a mixture of $N_2$+He—from pressure regulator 12 is conveyed through chilled-gas-supply tube 13 to the gas pre-cooling coil 14, preferably in the neck of the LN2 cryostat 5 for pre-cooling by the boil-off gas, according to the prior art.

The inlet pressure to the gas pre-cooling coil 14 typically needs to be 150-400 kPa, with the precise regulated pressure normally determined by the needs of the instrument, often an MAS-DNP probe.

The pre-cooled gas then proceeds to secondary-cooling coil 15 that is immersed in the LN2 in the cryostat, similar to the prior art. Coil 15 is sized such that heat transfer is insufficient to bring the mean temperature of the gas leaving this coil below approximately 4 K above the dew point of $N_2$ in this gas stream. For example, if the chilled gas stream is pure $N_2$ at 220 kPa, its dew point is 84 K. For this case, the mean temperature of the gas leaving coil 15 should be greater than 88 K. A typical mean exit temperature may be 120 K, but it could sometimes even be above 200 K. This non-condensing requirement sets upper limits on the heat transfer rate of the secondary-cooling coil 15 which depend mostly on required operating flow rate. Its heat transfer rate must be less than needed to produce significant liquid fraction in the chilled-gas stream. A typical I.D. would be 1-4 mm and a typical length would be 0.03-0.3 m. The heat transfer rate would typically need to be in the range of 10-200 W, depending largely on the flow rate needed for the chilled gas stream. The external surface area of this coil will typically be in the range of 2-200 $cm^2$.

Satisfactory operation can be achieved over an extremely wide range of flow and heat transfer conditions, as the chilled gas can leave the secondary cooling at any temperature above its saturated vapor temperature and still arrive at the input to the instrument needing cold gas at the desired temperature—over a very wide range—if the proper amount of LN2 is fed into the condensing coil. The required feed rate into that stream can easily be achieved, as described earlier, over the full range from zero to some upper limit, which can exceed the flow rate of the chilled gas stream.

It is important to appreciate that there will often be highly localized condensation and boiling inside coil 15, but the vapor fraction exiting this coil should be 100%.

This chilled-gas stream is then ducted up through a vacuum-insulated outlet line 16 to a suitable insulated right-angle coupling 17 at the top of the cryostat. The LN2 stream from the liquefaction coil 6 is injected from duct 7 into the gas stream at some point 18 beyond the bend in this coupling. The combined mixed-phase cold stream then flows through the transfer line 21 to an inlet port 22 on the instrument. During this transfer, the liquid phase boils, reducing the temperature of the gas phase and balancing heat leaks. To minimize problems with flow instabilities, the two-phase mixture must be at least 99% vapor fraction before it enters restrictive orifices 23 in the instrument—such as spinner bearing orifices or drive nozzles—where the majority of the pressure drop occurs. The vapor fraction may be less than 99% between inlet port 22 and orifices 23 if the vapor flow velocity is insufficient to entrain larger liquid droplets with it and if a control system is sufficiently responsive to insure that negligible liquid phase reaches the orifices 23.

Limiting Stored Nitrogen in the Condensing Flows. To minimize oscillations, the total amount of nitrogen stored in the liquefaction stream needs to be minimal—such that the total flow time from the needle valve 1 to the ultimate restrictive orifices 23 is preferably less than 30 seconds. This requires using lines that are not much larger than needed for acceptable pressure drops. The liquefaction-supply tube 3 would typically be 2-10 meters in length and would typically have I.D. of 2-4 mm. The precooling coil 4 would typically have I.D. of 1-3 mm and typical length of 0.3-2 m. The condensing coil 6 and LN2 duct 7 would typically have I.D. of 0.4-2 mm and typical length of 0.3-3 m.

Down-Hill Inhomogeneous Flow of the Mixed Phase. The largest contribution to liquid storage (hence, control difficulties) in the cold gas stream can arise from variability in liquid hold-up past the LN2 injection point. This is more easily minimized if the flow is downhill after the point of liquid injection 17, at least where flow velocities are low. The transfer line 21 can be supported so that the flow is downhill all the way from the injection point 18 to the inlet port 22 on the MAS probe.

The LN2 duct 7 carries the LN2 leaving condensing coil 6 up through the dewared outlet line 16 (also carrying the chilled gas) around the bend in the coupling 17 for injection into the chilled gas stream after the bend to prevent injected LN2 from running back and pooling in secondary cooling coil 15.

Some liquid would begin boiling inside the LN2 line prior to the injection point 18, so the injection might be 5-20% vapor fraction, but that has no substantive effect as long as the pressure drop is not excessive. Its mass flow rate and total cooling capacity are firmly established by valve 1, but some of its cooling of the chilled-gas stream will occur prior to its mixing with the chilled gas stream.

The external heat leaks (primarily in coupling 17) prior to the LN2 injection point will warm the chilled gas a little, but after the LN2 injection, the chilled gas will quickly be cooled to near the boiling point of nitrogen at its pressure in transfer line 21. The liquid fraction in the mixed-phase flow mid-way through transfer line 21 will typically be over 5% when lowest stable temperatures are desired entering the instrument orifices 23. The vapor or liquid fractions in this transfer line are actually not well defined, as they may be at substantially different flow velocities and the standard definitions assume the liquid flow is fully entrained within a macroscopically homogeneous flow.

Some LN2 may pool within the inlet port 22. The vapor phase bubbling through this will loft droplets, some of which may be small enough to be carried upward past a temperature control heater 24 toward the restrictive orifices 23. Control problems are manageable as long as the droplets are small enough that they vaporize (as the vapor temperature rises due to heat leaks) before reaching the orifices 23. In this way, most of the heat leaks in the transfer line within the probe may be balanced. The maximum size of the droplets is determined predominately by the vapor velocity and Stokes law. For cold nitrogen vapor at a velocity of 2 m/s and other typical conditions. for example, the maximum steadily lofted droplet size would be about 0.3 mm.

Figure 3:
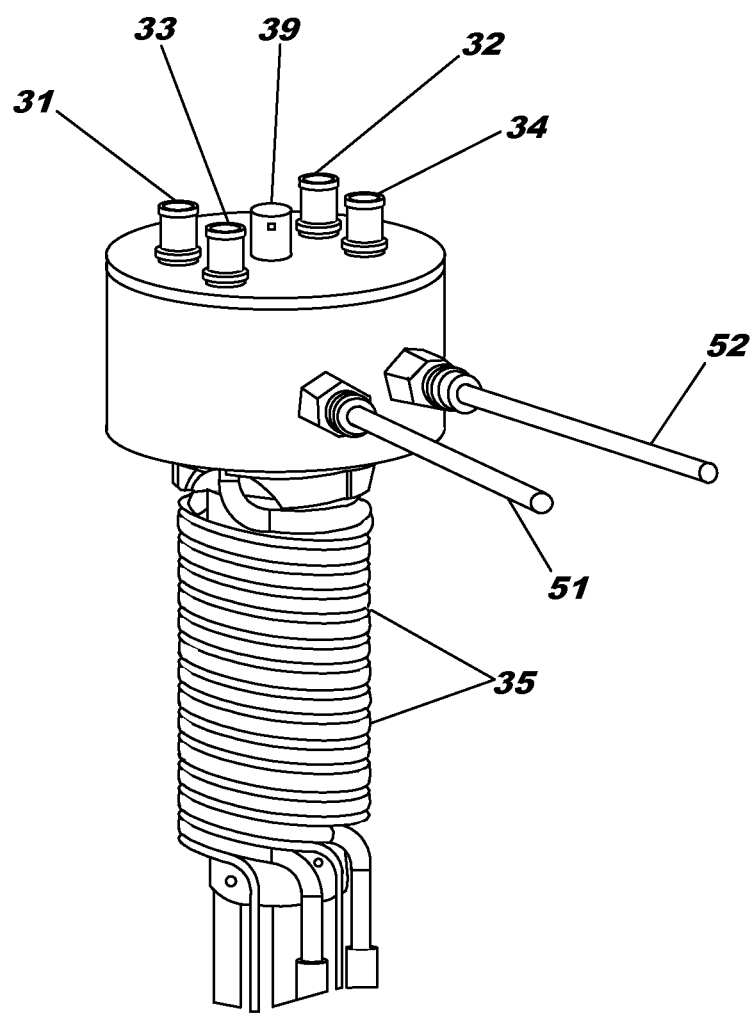
FIG. 3 shows a particular implementation of four pre-cooling coils.

Dual Saturated Streams. Thus far, the innovative method has been described with reference to production of a single controlled stream of saturated vapor from two source streams. For the MAS application, this would often be doubled, so as to produce two controlled streams of saturated vapor—one for the spinner bearing supply and one for the drive supply. Four precooling coils are needed, and a particular implementation for such is shown in FIG. 3. RT gas inlets 31, 32, 33, 34, one to each pre-cooling stream, are shown on the top of the core assembly. One of these goes to the top of the bearing gas precooling coil, one to the top of the bearing liquefaction precooling coil, one to the top of the drive gas precooling coil, and one to the top of the drive gas liquefaction precooling coil. The four precooling coils 35 may be of different sizes, as shown, and they are sized to fit conveniently into the neck of a standard LN2 cryostat, so cold boil-off $N_2$ gas flows over their surfaces. A fill port 39 may be included for filling the cryostat with liquid nitrogen. The two controlled saturated streams, produced separately from the combination of a gas and liquid stream by the method described earlier, exit from the sides of the assembly through insulated couplings 51, 52 for transfer to the instrument requiring such.

Figure 4:
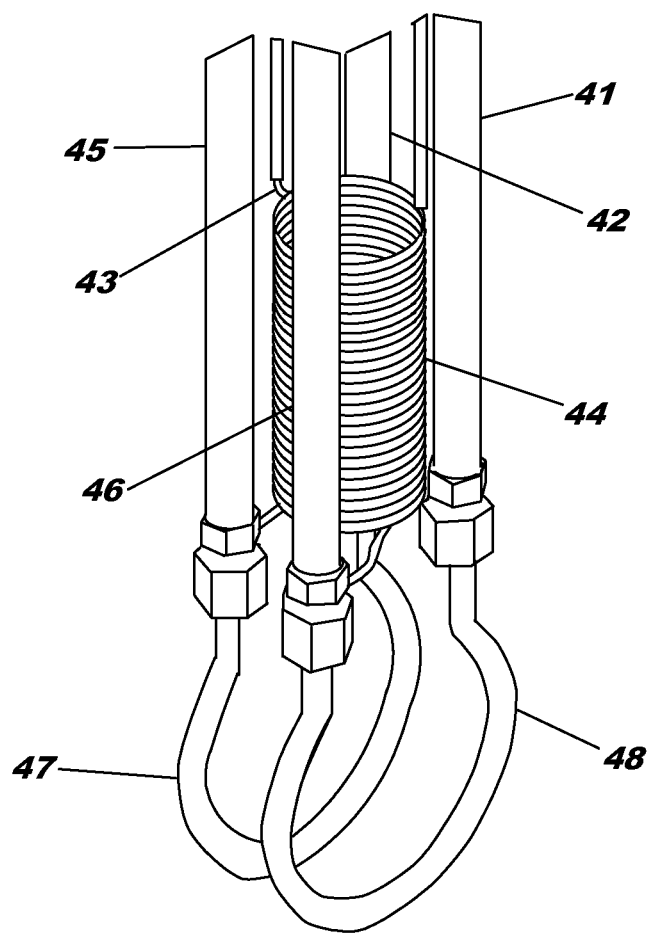
FIG. 4 shows a particular implementation of two condensing coils and two secondary cooling coils.

A particular implementation of two condensing coils and two secondary cooling coils, for immersion into the LN2 below the precooling coil assembly of FIG. 3, is shown in FIG. 4. The condensed LN2 leaving the bottom of each condensing coil 43, 44 is ducted into a vacuum insulated line 45, 46 along with gas leaving a secondary cooling coil 47, 48, though which the two controlled phases flow back to the couplings 51, 52 at top of the core assembly of FIG. 3. To minimize unwanted and variable additional heat transfer from the chilled gas stream to the LN2 in the cryostat, the lines 41, 42 from the pre-cooling coils to the secondary cooling coils are also vacuum insulated.

Helium-Nitrogen Mixtures for Faster Spinning at Lower Temperatures. The maximum stable spinning speed in an MAS spinner is primarily determined by the total pressure, density, and viscosity of the gas at the spinner, but the minimum temperature will be determined by the nitrogen partial pressure—as long as sufficient liquid nitrogen has been injected to achieve the needed cooling. So it will often be possible (depending on the spinner design) to achieve faster spinning at lower temperatures by using a helium-nitrogen mixture for the gases, thereby reducing the partial pressure of $N_2$ and hence its boiling point. Hence, a mixture of $N_2$ and He may be desired to supply the source gas to the pressure regulator 12 for the chilled gas stream. However, the liquefaction stream 3 would always be pure nitrogen.

Although this invention has been described herein with reference to specific embodiments, it will be recognized that changes and modifications may be made without departing from the spirit of the present invention. All such modifications and changes are intended to be included within the scope of the following claims.

The invention claimed is:
1. A cold gas supply system for use with a liquid nitrogen bath, the liquid nitrogen bath having vapor therefrom, the system comprising:
   a first pre-cooling coil for cooling a first pressurized gas stream by heat exchange with the vapor from the liquid nitrogen bath, said first pressurized gas stream comprised substantially of nitrogen,
   said bath contained in a cryostat having liquid capacity greater than 10 liters and less than 300 liters, the cryostat having a top,
   a condensing coil immersed in said bath to substantially condense said first pressurized gas stream to produce a pressurized liquid nitrogen stream,
   a second pre-cooling coil for cooling a second pressurized gas stream by heat exchange with the vapor from said bath to produce a pre-cooled second pressurized gas stream, said second pressurized gas stream comprised of nitrogen and helium of any ratio,
   a secondary cooling coil immersed in said bath to further cool said second pre-cooled second pressurized gas stream to produce a chilled gas stream, the chilled gas stream having a saturated vapor temperature,
   a first vacuum-insulated line for conveying the pre-cooled second pressurized gas stream from said second pre-cooling coil to said secondary cooling coil,
   a second vacuum-insulated line for conveying the chilled gas stream from said secondary cooling coil upward toward the top of said cryostat,
   a duct that injects said pressurized liquid nitrogen stream into said chilled gas stream,
   said secondary cooling coil further characterized as having heat transfer rate less than needed to cool said chilled gas stream below its saturated vapor temperature.

\* \* \* \* \*